United States Patent
Farag et al.

(10) Patent No.: US 8,014,561 B2
(45) Date of Patent: Sep. 6, 2011

(54) VIRTUAL FLY OVER OF COMPLEX TUBULAR ANATOMICAL STRUCTURES

(75) Inventors: Aly A. Farag, Louisville, KY (US); M. Sabry Hassouna, Eden Prairie, MN (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1034 days.

(21) Appl. No.: 11/899,451

(22) Filed: Sep. 6, 2007

(65) Prior Publication Data

US 2008/0069419 A1    Mar. 20, 2008

Related U.S. Application Data

(60) Provisional application No. 60/842,850, filed on Sep. 7, 2006.

(51) Int. Cl.
*G06K 9/00* (2006.01)
*A61B 5/05* (2006.01)
*A61B 8/00* (2006.01)

(52) U.S. Cl. .......................... 382/100; 600/407; 600/443

(58) Field of Classification Search .......... 382/128–134; 600/607, 425, 443, 449, 587; 602/63, 901
See application file for complete search history.

(56) References Cited

U.S. PATENT DOCUMENTS

| | | | |
|---|---|---|---|
| 6,928,314 B1 * | 8/2005 | Johnson et al. | 600/407 |
| 7,133,041 B2 * | 11/2006 | Kaufman et al. | 345/419 |
| 7,167,180 B1 * | 1/2007 | Shibolet | 345/474 |
| 2004/0209234 A1 | 10/2004 | Geiger | |
| 2005/0119550 A1 | 6/2005 | Serra et al. | |
| 2007/0003131 A1 | 1/2007 | Kaufman | |
| 2007/0071297 A1 | 3/2007 | Geiger et al. | |
| 2007/0103464 A1 | 5/2007 | Kaufman et al. | |

OTHER PUBLICATIONS

Anna Vilanova Bartroli et al., "Nonlinear Virtual Colon Unfolding", *IEEE*, 2001, pp. 411-418.

(Continued)

*Primary Examiner* — Abolfazl Tabatabai
(74) *Attorney, Agent, or Firm* — Greer, Burns & Crain Ltd.

(57) ABSTRACT

An embodiment of the invention is method, which can be implemented in software, firmware, hardware, etc., for virtual fly over inspection of complex anatomical tubular structures. In a preferred embodiment, the method is implemented in software, and the software reconstructs the tubular anatomical structure from a binary imaging data that is originally acquired from computer aided tomography scan or comparable biological imaging system. The software of the invention splits the entire tubular anatomy into exactly two halves. The software assigns a virtual camera to each half to perform fly-over navigation. Through controlling the elevation of the virtual camera, there is no restriction on its field of view (FOV) angle, which can be greater than 90 degrees, for example. The camera viewing volume is perpendicular to each half of the tubular anatomical structure, so potential structures of interest, e.g., polyps hidden behind haustral folds in a colon are easily found. The orientation of the splitting surface is controllable, the navigation can be repeated at another or a plurality of another split orientations. This avoids the possibility that a structure of interest, e.g., a polyp that is divided between the two halves of the anatomical structure in a first fly over is missed during a virtual inspection. Preferred embodiment software conducts virtual colonoscopy fly over. Experimental virtual fly over colonoscopy software of the invention that performed virtual fly over on 15 clinical datasets demonstrated average surface visibility coverage is 99.59+/−0.2%.

11 Claims, 4 Drawing Sheets

OTHER PUBLICATIONS

Christopher F. Beaulieu et al., "Display Modes for CT Colonography", *Radiology*, vol. 212, No. 1, Jul. 1999, pp. 203-212.

Ingmar Bitter et al., "Penalized-Distance Volumetric Skeleton Algorithm", *IEEE Transactions on Visualization and Computer Graphics*, vol. 7, No. 3, Jul.-Sep. 2001, pp. 195-206.

Sylvain Bouix et al., "Flux Driven Fly Throughts", *IEEE Computer Society Conference on Computer Vision and Pattern Recognition*, 2003.

Jen-Hui Chuang et al., "Skeletonization of Three-Dimensional Object using Generalized Potential Field", *IEEE Transactions on Pattern Analysis and Machine Ingtelligence*, vol. 22, No. 11, Nov. 2000, pp. 1241-1251.

Thomas Deschamps et al., "Fast Extraction of Minimal Paths in 3D Images and Applications to Virtual Endoscopy", *Medical Image Analysis*, vol. 1, 2001, pp. 1-19.

Nikhil Gagvani et al., "Parameter Controlled Volume Thinning", *Graphic Models and Image Processing*, May 1999, pp. 1-15.

Steven Haker et al., "Nondistorting Flattening Maps and the 3D Visualization of Colon CT Images", *IEEE Trans. on Medical Imaging*, vol. 19, No. 7, 2000, pp. 665-671.

M. Sabry Hassouna et al., "PDE-Based Three Dimensional Path Planning for Virtual Endoscopy", Presented in Proc. of Information Processing in Medical Imaging, IPMI, Glenwood Springs, Colorado, 2005.

M. Sabry Hassouna et al., "Differential Fly-Throughs (DFT): A General Framework for Computing Flight Paths", Presented in MICCAI, Palm Springs, CA Oct. 26-29, 2005.

Taosong He et al., "Reliable Path for Virtual Endosocpy: Ensuring Complete Examination of Human Organs", *IEEE Transactions on Visualization and Computer Graphics*, vol. 7, No. 4, Oct.-Dec. 2001, pp. 333-342.

Wei Hong et al., "Conformal Virtual Colon Flattening", ACM Symposium on Solid and Physical Modeling,Proceedings of the 2006 ACM symposium on Solid and physical modeling, 2006.

Dong-Goo Kang et al., "A New Path Planning Algorithm for Maximizing Visibility in Computed Tomography Colonography", *IEEE Transactions on Medical Imaging*, vol. 24, No. 8, Aug. 2005, pp. 957-968.

David Seungwon Paik, "Computer Aided Interpretation of Medical Images", Aug. 2002.

Alexandru Telea et al., "A Robust Level-Set Algorithm for Centerline Extraction", *IEEE TCVG Symposium on Visualization*, 2003.

Frans M. Vos et al., "Three-Dimensional Display Modes for CT Colonography: Conventional 3D Virtual Colonoscopy versus Unfolded Cube Projection", *Radiology*, vol. 228, No. 3, pp. 878-885.

Yong Zhou et al., "Efficient Skeletonization of Volumetric Objects", *IEEE Transactions on Visualization and Computer Graphics*, vol. 5, No. 3, 1999, pp. 196-209.

\* cited by examiner

VIRTUAL FLY OVER OF COMPLEX TUBULAR ANATOMICAL STRUCTURES

PRIORITY CLAIM AND REFERENCE TO RELATED APPLICATION

This application claims priority pursuant to 35 U.S.C. §120 from prior provisional application Ser. No. 60/842,850, filed Sep. 7, 2006.

FIELD

A field of the invention is medical imaging. Example applications of the invention include virtual colonoscopy. In general, the invention can be used to virtually inspect complex tubular anatomical structures, e.g., the colon & arteries.

BACKGROUND

Techniques for the examination of tubular anatomical structures, such as the trachea, arteries, colon, digestive tract, etc., are important procedures for detecting abnormalities. Such abnormalities can include polyps, the latter of which are indicators of developing cancer. For example, optical colonoscopies are an important procedure to detect polyps that are early stage indicators of cancer.

Colorectal colon cancer is the third most common form of cancer and the second leading cause of death among cancers in the western world. Since colorectal cancer is largely preventable, the colonoscopy screening test is recommended for all people age 50 and over. Although optical colonoscopy detects more than 90% of colorectal cancers, it is invasive, uncomfortable, inconvenient, and sometimes can not reach the colon caecum, resulting in an incomplete exam.

As a result, researchers have been investigation virtual colonoscopy (VC) as a computer-based alternative to optical colonoscopy. VC is generally not intended to replace optical colonoscopy, but rather to complement it by providing additional supportive information such as visualizing in both directions, passing high grade stenoses, and planning for surgery. In addition, it is the only alternative offered to those patients that are not comfortable with optical colonoscopy or are severely ill.

The common visualization technique that tries to simulate the real colonoscopy is the virtual fly-through navigation, where a virtual camera with a specific field of view moves along a special planned path inside the colon to render its internal views. The direction of navigation either starts from the colon rectum side (antegrade), or from its caecum side (retrograde). In general, fly-through based-methods suffer from the following limitations: (1) the camera's field of view is limited, and hence results in lower surface visibility coverage; and (2) the navigation must be done in both antegrade and retrograde directions to maximize visualized surface areas, and hence it is very time consuming. Several other visualization techniques have been proposed to overcome those shortcomings, which can be categorized as colon flattening and panoramic methods. The main idea behind colon flattening methods is to initially transform the colon into a cylinder-like shape to reduce its overall tortuosity, and then to map the straightened colon onto a single image, which can be inspected from a single view point. Because flattening methods are based on geometric mapping, geometric distortion is inevitable. As a consequence, important diagnostic features can be altered or even eliminated.

There are a number of panoramic methods. The methods divide the colon into a plurality of views. One of the main drawbacks of this method is that a polyp may split among several of the rendered views. In addition, the layout of several views, such as an unfolded cube is hard to follow, since a medical professional must observe views simultaneously that are sometimes oriented in different directions (horizontal and vertical). Other panoramic methods induce distortion and all have the potential to hide polyps behind haustral folds that can be easily overlooked under the following scenarios: (1) A polyp is located along the camera optical axis, and hence its depth perception is lost by a physician; or (2) A polyp is completely blocked by a haustral fold.

SUMMARY OF THE INVENTION

An embodiment of the invention is method, which can be implemented in software, firmware, hardware, etc., for virtual fly over inspection of complex anatomical tubular structures. In a preferred embodiment, the method is implemented in software, and the software reconstructs the tubular anatomical structure from a binary imaging data that is originally acquired from computer aided tomography scan or comparable biological imaging system. The software of the invention splits the entire tubular anatomy into exactly two halves. The software assigns a virtual camera to each half to perform fly-over navigation. Through controlling the elevation of the virtual camera, there is no restriction on its field of view (FOV) angle, which can be greater than 90 degrees, for example. The camera viewing volume is perpendicular to each half of the tubular anatomical structure, so potential structures of interest, e.g., polyps hidden behind haustral folds in a colon are easily found. The orientation of the splitting surface is controllable, the navigation can be repeated at another or a plurality of another split orientations. This avoids the possibility that a structure of interest, e.g., a polyp that is divided between the two halves of the anatomical structure in a first fly over is missed during a virtual inspection. Preferred embodiment software conducts virtual colonoscopy fly over. Experimental virtual fly over colonoscopy software of the invention that performed virtual fly over 15 clinical datasets demonstrated average surface visibility coverage is 99.59+ 0.2%

DETAILED DESCRIPTION OF THE PREFERRED EMBODIMENTS

An embodiment of the invention is method, which can be implemented in software, firmware, hardware, etc., for virtual fly over inspection of complex anatomical tubular structures. In a preferred embodiment, the method is implemented in software, and the software reconstructs the tubular anatomical structure from a binary imaging data that is originally acquired from computer aided tomography scan or comparable biological imaging system. The software of the invention splits the entire tubular anatomy into exactly two halves. The software assigns a virtual camera to each half to perform fly-over navigation. Through controlling the elevation of the virtual camera, there is no restriction on its field of view (FOV) angle, which can be greater than 90 degrees, for example. The camera viewing volume is perpendicular to each half of the tubular anatomical structure, so potential structures of interest, e.g., polyps hidden behind haustral folds in a colon are easily found. The orientation of the splitting surface is controllable, the navigation can be repeated at another or a plurality of another split orientations. This avoids the possibility that a structure of interest, e.g., a polyp that is divided between the two halves of the anatomical structure in a first fly over is missed during a virtual inspection. Preferred embodiment software conducts virtual colonoscopy fly over. Experimental virtual fly over colonoscopy software of the invention that performed virtual fly over 15 clinical datasets demonstrated average surface visibility coverage is 99.59±0.2%.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

Figure 1:
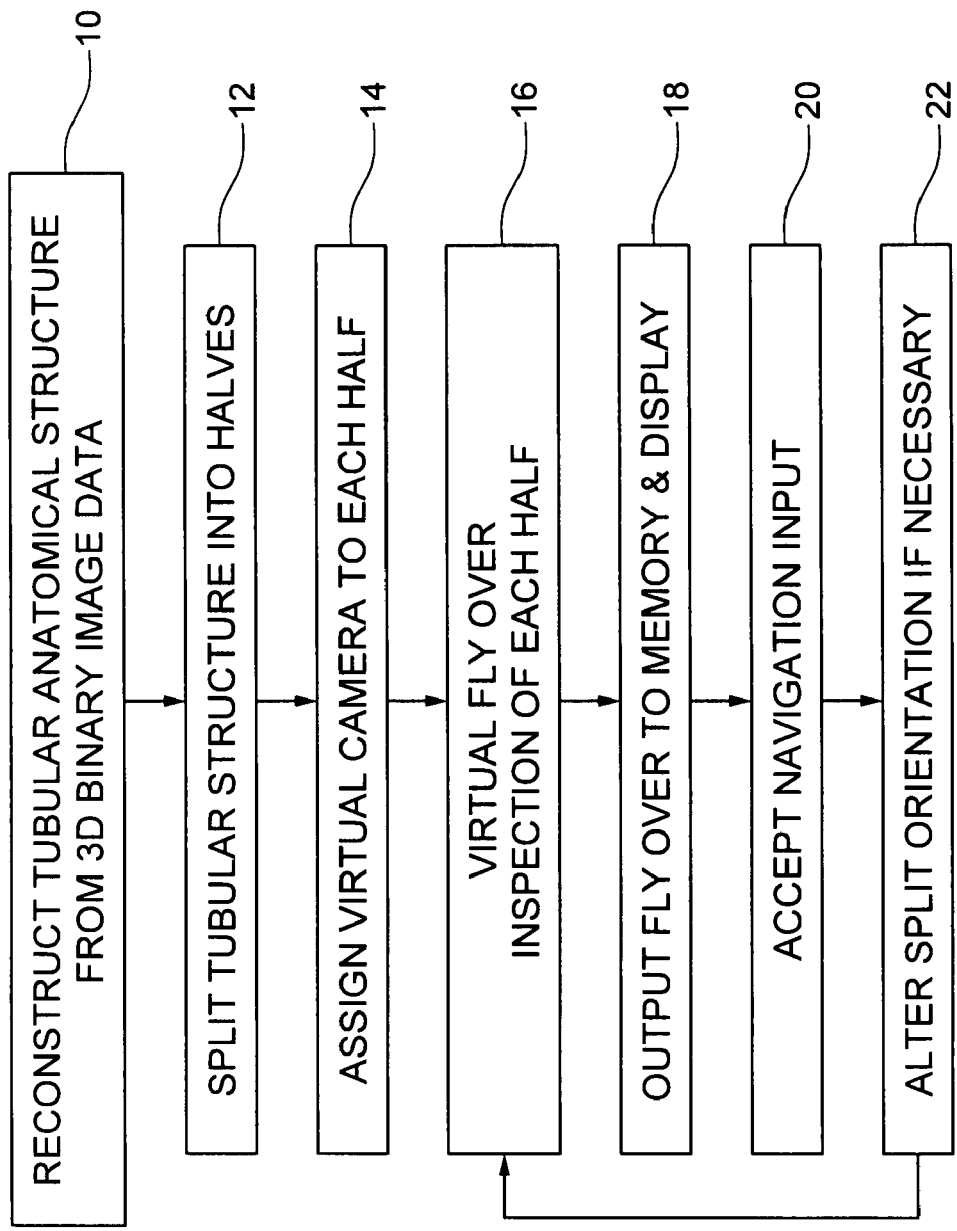
FIG. 1 is a schematic diagram showing operations of preferred embodiment software of the invention.

FIG. 1 is a schematic diagram showing major operations of preferred embodiment method and software of the invention. The method of FIG. 1 can be encoded into software or firmware in any conventional manner, programming language, operating system, embedded in hardware, etc. The software can be located on a stand alone computer or accessed over a local or wide area network, for example. The software reconstructs 10 a tubular anatomical structure from 3D binary imaging data, e.g., a colon. The software splits 12 the entire tubular anatomy into exactly two halves. A virtual camera is assigned 14 to each of the two halves. A virtual fly over inspection of each of the two halves is conducted 16 while controlling the elevation of the virtual camera such that the camera viewing volume is perpendicular to each half of two halves. The software preferably outputs 18 the virtual fly over to memory and display permitting a medical professional, typically a doctor, to view the virtual fly over. Additionally, the software preferably accepts navigation input 20 from an interface provided to the medical professional to interactively control the virtual fly over. This permits the medical professional, for example, to control the speed of the fly over and to pause, go back and go forward to various points in the virtual fly over. Additionally, the software further preferably includes code for changing 22 an orientation used in the splitting 12 to permit an additional fly over at a different split orientation. Multiple split orientations and fly overs are preferred to ovoid the possibility that a first split of the tubular structure split a structure of interest, e.g., a polyp in a colon. By using multiple split orientations and fly overs, the possibility of splitting polyps can be avoided.

Figure 2:
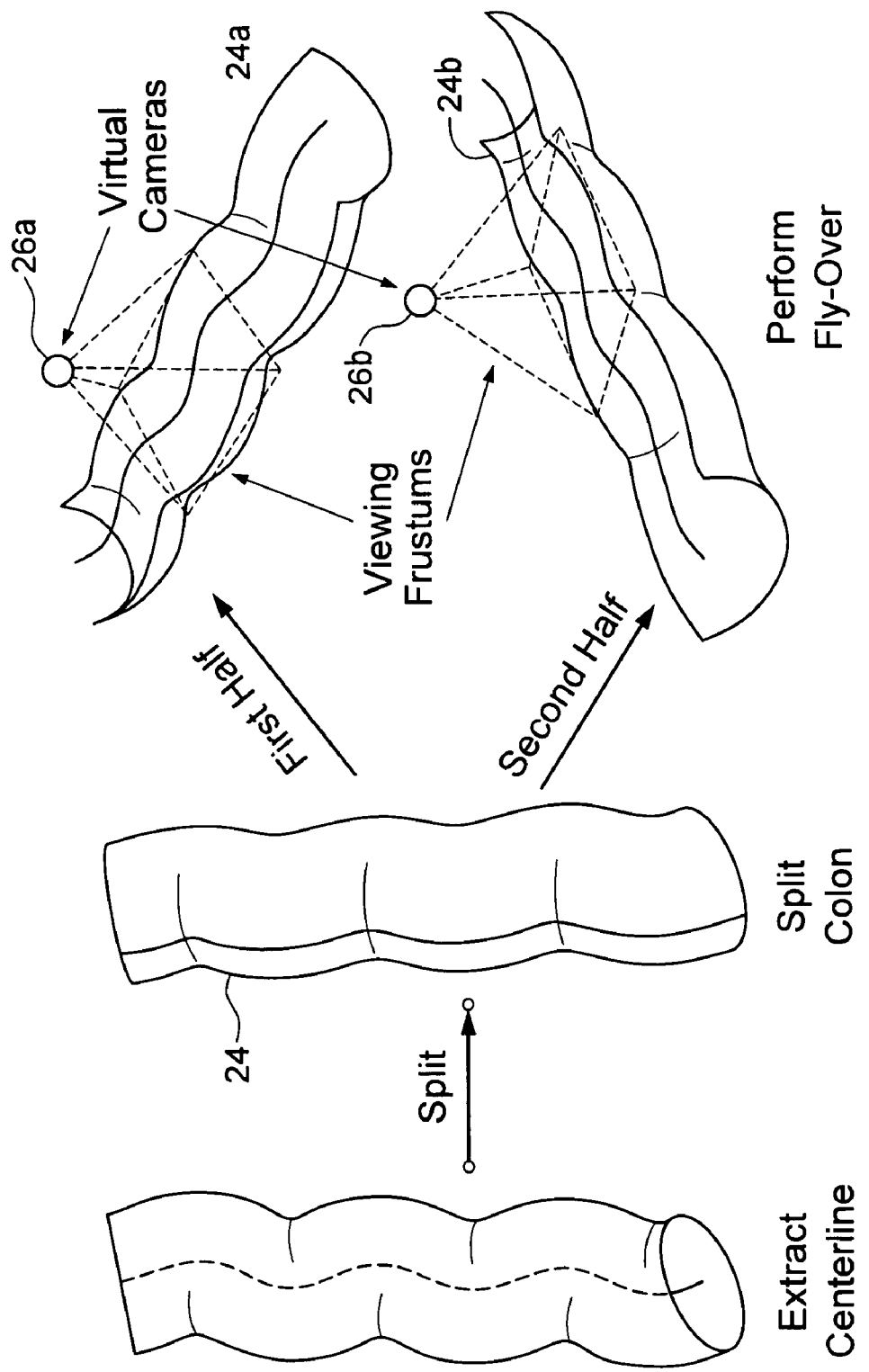
FIG. 2 graphically illustrates the operations of the software of FIG. 1.

The operations are graphically illustrated in FIG. 2 with respect to a colon 24. The colon is split into halves 24a and 24b. Respective virtual cameras 26a and 26b are to the colon halves 24a and 24b, and a virtual fly over is conducted.

Details of a preferred virtual colonoscopy embodiment will now be discussed with respect to FIG. 3. Artisans will appreciate that the specific operations are also applicable to image data of other complex tubular biological objects, e.g., the trachea, arteries, etc. Initially the colon lumen is segmented using a seeded region growing algorithm. The splitting 12 involves first obtaining the centerline of the colon. Centerline extraction is discussed in co-pending patent application Ser. No. 11/823,738, filed Jun. 28, 2007, and entitled METHOD AND SOFTWARE FOR SHAPE REPRESENTATION WITH CURVE SKELETONS. Centerline extraction is also disclosed in Hassouna, M. S., Farag, A., Falk, R., "Differential fly-throughs (dft): A general framework for computing flight paths." MICCAI, Palm Springs, Calif., Oct. 26-29, 2005. Other methods can also be used to extract the centerline, and those methods that extract the centerline with high accuracy are preferred, for example, I. Bitter, A. E. Kaufman, and M. Sato. "Penalized-distance volumetric skeleton algorithm," IEEE Transactions on Visualization and Computer Graphics, pp. 195-206, 2001. Other example centerline extraction methods are discussed in the following publications: S. Bouix, K. Siddiqi, and A. Tannenbaum. "Flux driven fly throughs," In Proc Computer Vision and Pattern Recognition, pp. 449-454, June 2003; J.-H. Chuang, C.-H. Tsai, and M.-C. Ko. "Skeletonization of three-dimensional object using generalized potential field," IEEE Transaction on Pattern Analysis and Machine Intelligence, vol. 22, no. 11, pp. 1241-1251, 2000; T. Deschamps and L. Cohen. "Fast extraction of minimal paths in 3d images and applications to virtual endoscopy," Medical Image Analysis, 5(4), pp. 281-299, 2001.

After the centerline is extracted, the splitting preferably involves applying a polygonal clipping surface 28 that passes through the colon's centerline. Approximating the polygonal surface by the union of finite size planes is not suitable because clipping needs to be accomplished by implicit surfaces such as a sphere, cube, cylinder, or an infinite plane. However, on an object such as the colon, applying a polygonal clipping surface 28 is a computational intensive process. A preferred simplification of the polygonal clipping is to divide the colon surface into consecutive strips of triangles (rings) 30. Each ring is then split into two halves by an infinite plane that passes along its local centerline 32. Each set of consecutive half rings are concatenated altogether to form one half of the colon 34. Finally, the colon's surface is reconstructed in 3D 36, preferably using the well-known marching cubes algorithm or later variants. Details of the marching cubes algorithm are discussed, for example, in Lorensen, W. E., Cline, H. E.: "Marching cubes: A high resolution 3d surface construction algorithm." Proc. of SIGGRAPH. (1987) 163-169; Also see, U.S. Pat. No. 4,710,876, which issued Dec. 1, 1987. A related technique is referred to as the dividing cubes technique and is disclosed in U.S. Pat. No. 4,719,585, which issued Jan. 12, 1988.

1. Generation of Rings

Figure 4A:
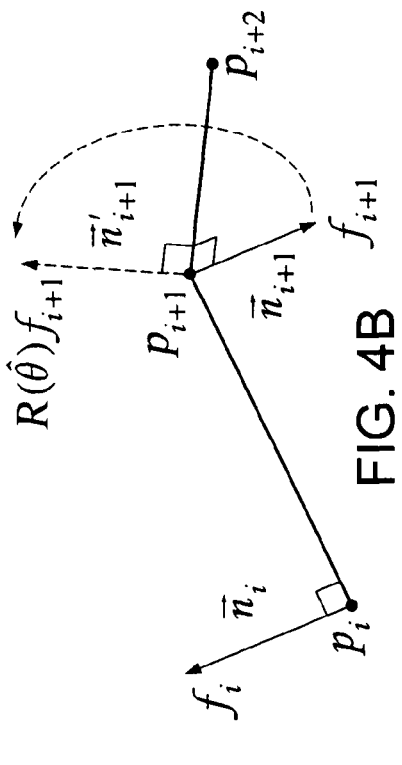
FIGS. 4A-4C illustrate mathematical modeling for sampling of a colon centerline and the pin-hole model of the virtual camera.

Let C be a smoothed version of the colon's centerline, which is sampled uniformly to $N_p$ points as shown in FIG. 4A. Each point $p_i$, where $1 \leq i \leq N_p$ is associated with a tangential vector $\vec{t}_i$ and a normal vector $\vec{n}_i$. The centerline C is also divided into $N_s$ segments $l_j$, where $1 \leq i \leq N_s$. Each segment $l_j$ is 1 cm in length (e.g., 20 voxels for 0:5 mm voxel size). The points of each segment $l_j$ are assigned a specific label based on the following label function $$\forall p_i \in l_j, \text{label}(p_i) = j \tag{1}$$

To divide the colon surface into consecutive rings, a surface skinning method can be used, where each mesh triangle is assigned the label of the nearest centerline segment $l_j$. As a consequence, the set of surface triangles of the same label form a ring. Let $c_k$ be the geometric center of each surface triangle $r_k$, where $1 \leq i \leq N_r$ and $N_r$ is the total number of surface triangles. Then, the skinning process is governed by the following equation.

$$\hat{p}_i = \arg\min_{p_i \in C} \|c_k - p_i\|^2, \text{ label}(r_k) = \text{label}(\hat{p}_i) \quad (2)$$

Surface skinning is a fast process of computational complexity $O(N_r, N_p)$.

Figure 4B:
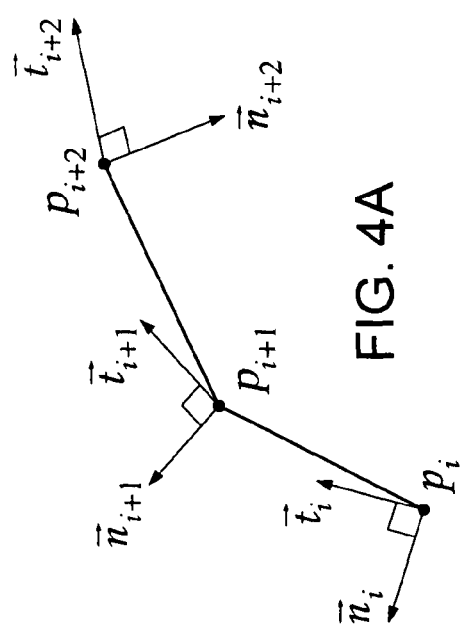
Figure 4C:
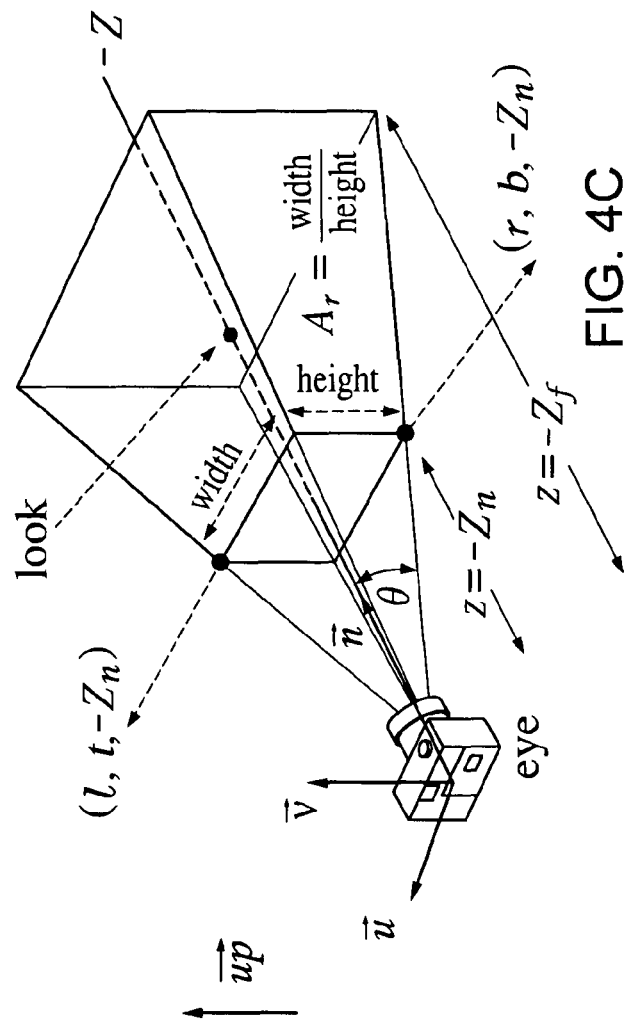

In FIG. 4B, the centerline C is uniformly sampled to $N_p$ points. Each point $f_{i+1}$ is rotated around the line segment that is given by the points $p_{i+1}$ and $p_{i+2}$ until the rotation angle between the normal vectors $n_{i+1}$ and $n_i$ is minimized. FIG. 4C shows the pinhole virtual camera model.

The steps in FIGS. 4A-4C divide the colon surface into a plurality of consecutive rings that correspond to the length of the centerline segments, e.g., $l_j > 1$ cm. The computed normals along the centerline may change their directions abruptly. Aligned normals provide a good approximation of the clipping surface. Changing the direction of the first normal vector results in a new split orientation surface.

2. Splitting Rings

Each ring $R_j$ spans multiple centerline points, whose starting and ending points are $q_j$ and $q_{j+1}$, respectively. To split $R_j$ into two halves, it is preferably clipped using an infinite plane $\pi_j$, whose center is $q_j$ and whose normal vector is given by $$\vec{u}_j = (q_{j+1} - q_k) \times \vec{n}_j \quad (3)$$

To generate the entire clipping planes along all rings, a first step is to compute the normal vectors along the centerline, which can be generated using a common method in computer graphics. Specifically, the normal vector $\vec{n}_i$ at each centerline point $p_i$ is given by, $$\vec{w}_i = \vec{up} \times \vec{t}_i, \vec{n}_i = \vec{t}_i \times \vec{w}_i \quad (4)$$

where, $\vec{up}$ is an arbitrary vector, which is adaptively chosen at each point to be any of the Cartesian basis vectors as long as it is not parallel to $\vec{t}_i$. Since the polygonal splitting surface is approximated by the union of finite size planes, then each two consecutive planes must share an edge, which implies that each two consecutive normal vectors $\vec{n}_i$ and $\vec{n}_{i+1}$ are in the same plane.

Due to the high tortuosity nature of the colon and hence its centerline, the generated normal vectors along the centerline using Eq. (4) can change their directions abruptly. This can be addressed as follows: Let $\vec{n}_i$ be described by the end points $p_i$ and $f_i$, while $\vec{n}_{i+1}$ by $p_{i+1}$ and $f_{i+1}$ as shown in FIG. 4B. Each point $f_{i+1}$ is rotated around the line segment that is given by the points $p_{i+1}$ and $p_{i+2}$ until the rotation angle between $\vec{n}_{i+1}$ and $\vec{n}_i$ is minimized, which can be formulated mathematically by the following optimization problem, $$\hat{\theta} = \arg\min_{\theta} \|f_i - R(\theta)f_{i+1}\|^2 \quad (5)$$

where $R(\theta)$ is the rotation matrix. This provides alignment of normal vectors of and permits splitting of the colon or another complex tubular anatomical structure into exactly two halves.

3. Controlling Split Orientation

Since each normal vector $\vec{n}_{i+1}$ is aligned with respect to the previous vector $\vec{n}_i$, then by changing the direction of the first normal vector $\vec{n}_1$, the rest of the normal vectors will change their orientations as well. Therefore, $\vec{n}_1$ controls the orientation of the split surface. For example, by rotating the first normal vector $\vec{n}_1$ of by 90°, a new split orientation is yielded.

4. Virtual Fly-Over

Each colon half is assigned a perspective virtual camera, whose model is shown in FIG. 4C. The part of the pyramid that is enclosed by the clipping planes $Z_n$ and $Z_f$ is called the viewing volume or frustum. The orientation of each camera is controlled by four parameters that are computed automatically during fly-over navigation. The parameters are the camera position vector $\vec{pos}$, the look-at vector $\vec{look}$, which describes the direction of projection, the view-up vector $\vec{up}$, and the field of view angle $\theta$. The look-at vectors of the first half (l=1) and second half (l=2) are given by, $$\vec{look}_{i,l=1} = \vec{t}_i \times \vec{n}_i, \vec{look}_{i,l=2} = -\vec{look}_{i,l=1} \quad (6)$$

The camera position and view-up vectors of each half are given as follows, $$\vec{pos}_{i,1} = p_i + h_i \frac{\vec{look}_{i,l}}{\|\vec{look}_{i,l}\|}, \vec{up}_{i,l} = \vec{t}_i \quad (7)$$

where $h_i$ is the camera elevation from each centerline point $p_i$. According to FIG. 2(c), the camera's FOV is given by, $$\tan\left(\frac{\theta}{2}\right) = \frac{\text{height}}{2Z_n} \quad (8)$$

During centerline extraction, each point $p_i$ encodes its distance from the colon's boundary $D(p_i)$. By making $p_i$ the focal point of the camera, where the image plane is located, then the elevation of the camera $h_i$ at each point $p_i$ that maximizes surface visibility coverage, while maintaining the same angle $\theta$ is given by, $$h_i = \frac{D(p_i)}{\tan(\theta/2)} \quad (9)$$

According to Eq. (9), there is no limitation on the FOV angle that maximizes surface visibility coverage. For example, for $\theta=90°$, $h_i=D(p_i)$, while for $\theta=60°$, $h_i=1:73\ D(p_i)$.

3. Quantitative Validation

To quantitatively validate the fly-over navigation of the invention in terms of effectiveness (surface visibility coverage), clinical datasets of 15 patients were acquired using Siemens Sensation CT scanner. The dataset volume is 512×512×580 with voxel size 0.74×0.74×0.75 mm³.

Table 1 compares the surface visibility coverage of the virtual fly over methods with a fly-through method; Hassouna, M. S., Farag, A., Falk, R., "Differential fly-throughs (dft): A general framework for computing flight paths." MICCAI, Palm Springs, Calif., Oct. 26-29, 2005. for three clinical datasets, while navigating in the antegrade, retrograde, and both directions at 90° FOV.

TABLE 1

Comparison of surface visibility by the
fly-over and fly-through methods.

| Navigation Direction | Navigation Technique | Surface Visibility (%) | | |
|---|---|---|---|---|
| | | Dataset A | Dataset B | Dataset C |
| Antegrade | Fly-through | 79.29 | 78.95 | 79.38 |
| | Fly-over | 99.35 | 99.68 | 99.33 |
| Retrograde | Fly-through | 77.89 | 75.74 | 79.00 |
| | Fly-over | 99.6 | 99.91 | 99.68 |
| Antegrade + Retrograde | Fly-through | 93.64 | 93.12 | 93.38 |
| | Fly-over | 99.7 | 99.95 | 99.73 |

4. Discussion and Conclusion

The validation experiment on 15 clinical datasets have shown that the surface visibility coverage by the present fly over method, irrespective of the navigation direction, is on average 99.59%±0.2. To ensure 100% surface coverage, invisible areas are clustered using a connected component algorithm and then properly visualized. Although panoramic methods have reported nearly the same surface visibility coverage, they still suffer from other limitations as discussed above. Testing has shown that fly-over navigation in either direction (antegrade or retro-grade) is sufficient for nearly complete surface coverage.

In testing some rendered views of both fly-through and fly-over are showed the same number of polyps, but the fly-over method also revealed is more polyps than other corresponding fly-through views. Evaluation time was on average 26 minutes by fly-through methods in both directions and 13 minutes (including 3 minutes for surface reconstruction, skinning, splitting, and rendering) by the present fly-over method on a 3 Ghz Pentium computer with 2 GB memory and an nVidia Quadro FX 3000 graphics card.

Due to the nature of the fly-over navigation, the viewing volume is perpendicular to each colon half, which results in higher surface visibility coverage and higher sensitivity. By controlling the elevation of the camera, there is no restriction on its FOV angle to maximize visualized surface area, and hence the present method does not suffer from perspective distortion. Because the split orientation is controllable, the navigation can be repeated at a different split orientation if a polyp is divided between the halves of a colon.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A method for virtual fly over inspection of complex tubular anatomical structures that exist in more than one plane, comprising steps for:
   reconstructing a tubular anatomical structure from a binary imaging data;
   splitting the entire tubular anatomical structure into exactly two halves without transformation of the tubular anatomical structure;
   assigning a virtual camera to each of the two halves; and
   conducting a virtual fly over inspection of each of the two halves while controlling the elevation of the virtual camera such that the camera viewing volume is perpendicular to each half of two halves.

2. The method of claim 1, further comprising steps for:
   outputting the virtual fly over inspect to a display;
   accepting navigation input to interactively control the virtual fly over.

3. The method of claim 1, wherein the method further includes a step of changing orientation used in said step of splitting such that said step of conducting can be repeated at another one or plurality of split orientations.

4. The method of claim 1, further comprising outputting the virtual fly over to memory.

5. A method for virtual fly over inspection of complex anatomical tubular structures, comprising steps for:
   reconstructing a tubular anatomical structure from a binary imaging data.
   splitting the entire tubular anatomical structure into exactly two halves;
   assigning a virtual camera to each of the two halves; and
   conducting a virtual fly over inspection of each of the two halves while controlling the elevation of the virtual camera such that the camera viewing volume is perpendicular to each half of two halves, wherein said step of splitting comprise steps of:
   dividing the tubular anatomical structure into consecutive rings;
   halving the consecutive rings into halves by passing an infinite plane through ring centerlines;
   concatenating consecutive half rings; and
   reconstructing the surface of the tubular anatomical structure.

6. The method of claim 5, wherein said step of reconstructing comprises applying marching cubes algorithm.

7. The method of claim 5, wherein said step of dividing comprise segmenting a centerline of the tubular anatomical structure into a plurality of segments and computing a normal to the centerline between each segment.

8. The method of claim 7, wherein said step of halving comprises aligning orientation of computed normals and passing the infinite plane through the centerline along the aligned normals to the centerline.

9. The method of claim 8, further comprising aligning computed normals at a second orientation and passing a second infinite plane through the centerline along the normals at the second orientation, and repeating said steps of assigning and conducting.

10. A non-transitory computer-readable medium encoded with a computer program for virtual fly over inspection of complex anatomical tubular structures, comprising code for:
    reconstructing a tubular anatomical structure from binary imaging data.
    computing a centerline of the tubular anatomical structure;
    segmenting the centerline of the tubular anatomical structure into a plurality of segments and computing a normal to the centerline between each segment;
    aligning orientation of computed normals and passing an infinite plane through the centerline along the aligned normals to the centerline to divide the tubular anatomical structure into halves;
    assigning a virtual camera to each of the two halves; and
    conducting a virtual fly over inspection of each of the two halves while controlling the elevation of the virtual camera such that the camera viewing volume is perpendicular to each half of two halves.

11. A method for virtual fly over inspection of complex anatomical tubular structures, comprising steps for:
    reconstructing a tubular anatomical structure from binary imaging data;
    computing a centerline of the tubular anatomical structure;

dividing a surface of the tubular anatomical structure into a plurality of consecutive rings;
splitting each of the consecutive rings into two halves along commonly aligned normals;
concatenating consecutive half rings and reconstructing the surface of the tubular anatomical structure and generate two halves;
conducting a virtual fly over inspection of each of the two halves while controlling the elevation of the virtual camera such that the camera viewing volume is perpendicular to each half of two halves.

* * * * *

UNITED STATES PATENT AND TRADEMARK OFFICE
CERTIFICATE OF CORRECTION

| | | |
|---|---|---|
| PATENT NO. | : 8,014,561 B2 | Page 1 of 1 |
| APPLICATION NO. | : 11/899451 | |
| DATED | : September 6, 2011 | |
| INVENTOR(S) | : Farag et al. | |

Figure 3:
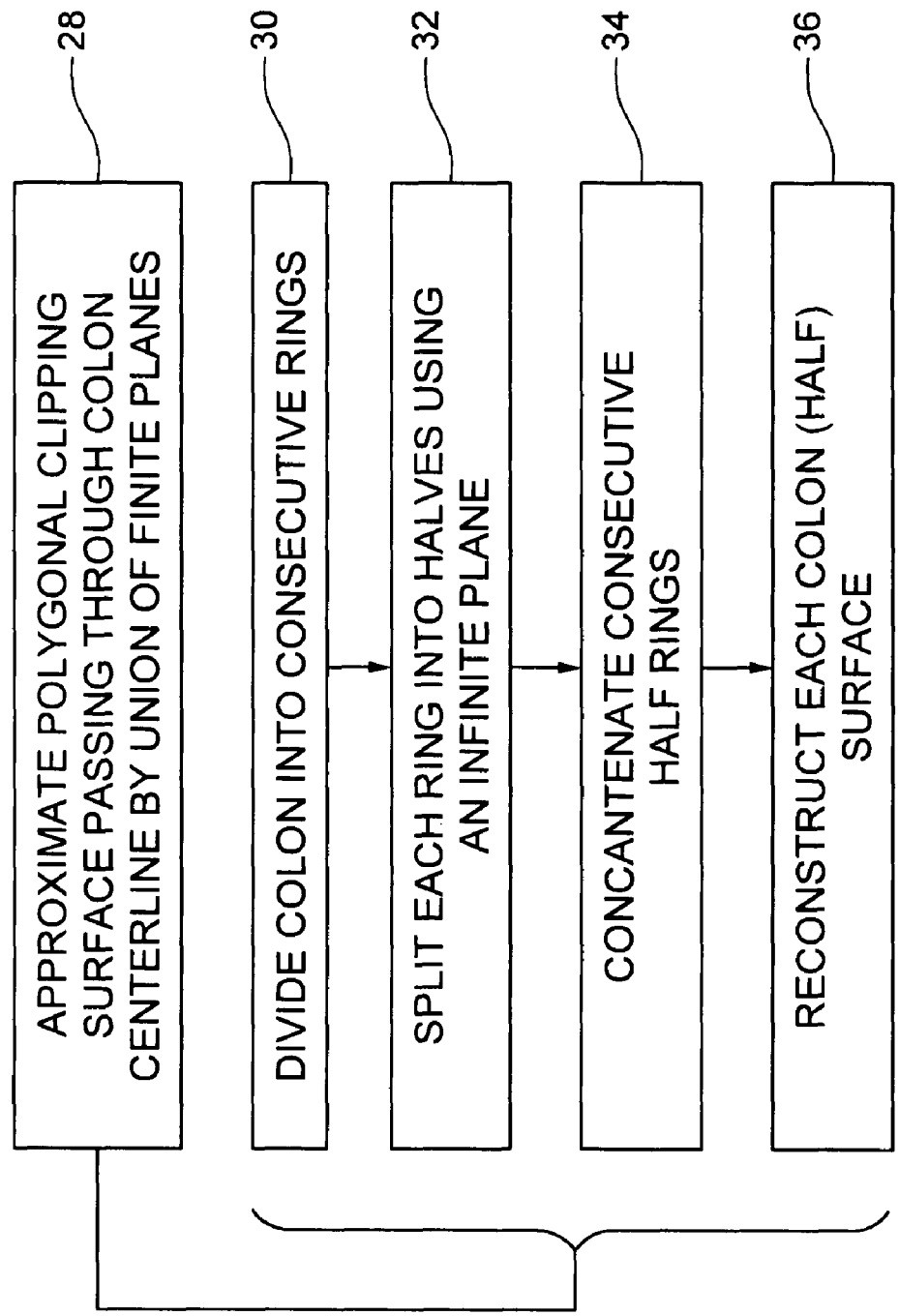
FIG. 3 is a schematic diagram showing operational details of the splitting operation of FIG. 1.

It is certified that error appears in the above-identified patent and that said Letters Patent is hereby corrected as shown below:

In the Drawings:

Sheet 3, FIG. 3     In box 34, please delete "CONCANTENATE" and insert --CONCATENATE-- therefor.

In the Specification:

Col. 1, line 35     Please delete "investigation" and insert --investigating-- therefor.

Col. 2, lines 40-41     Please delete "99.59+0.2%" and insert --99.59+/-0.2%-- therefor.

Col. 3, line 51     Please delete "ovoid" and insert --avoid-- therefor.

Col. 5, line 6     Please delete "$label(r_k = label(\hat{p}_i)$" and insert --$label(r_k = label(\hat{p}_i))$-- therefor.

Col. 5, line 13     Please delete "$P_i2$" and insert --$P_{i+2}$-- therefor.

Col. 5, line 30     Please delete "$\vec{u}_j=(q_{j+1}-q_k)\times\vec{n}_j$" and insert --$\vec{u}_j = (q_{j+1} - q_j) \times \vec{n}_j$-- therefor.

Col. 6, line 9     After "vector $\vec{n}_1$", please delete "of".

Col. 6, line 54     Please delete "$h_i=1:73D(p_i)$" and insert --$h_i=1:73\Delta(p_i)$-- therefor.

Col. 7, line 27     Please delete "In testing some" and insert --In testing, some-- therefor.

Col. 7, line 28     Please delete "fly-over are showed " and insert --fly-over showed-- therefor.

Col. 7, line 29     Please delete "revealed is more" and insert --revealed more-- therefor.

In the Claims:

Col. 9, lines 6-7
Claim 11, lines 11-12     Please delete "generate" and insert --generating-- therefor.

Signed and Sealed this
Twenty-eighth Day of February, 2012

David J. Kappos
*Director of the United States Patent and Trademark Office*